United States Patent
Zhao

(10) Patent No.: US 8,333,591 B2
(45) Date of Patent: Dec. 18, 2012

(54) BIONIC DENTAL IMPLANT

(76) Inventor: Daguo Zhao, Chengdu (CN)

( * ) Notice: Subject to any disclaimer, the term of this patent is extended or adjusted under 35 U.S.C. 154(b) by 263 days.

(21) Appl. No.: 12/595,270

(22) PCT Filed: Apr. 3, 2008

(86) PCT No.: PCT/CN2008/070674
§ 371 (c)(1),
(2), (4) Date: Oct. 9, 2009

(87) PCT Pub. No.: WO2008/125049
PCT Pub. Date: Oct. 23, 2008

(65) Prior Publication Data
US 2010/0055646 A1 Mar. 4, 2010

(30) Foreign Application Priority Data

Apr. 12, 2007 (CN) .......................... 2007 1 0048850

(51) Int. Cl.
*A61C 8/00* (2006.01)
(52) U.S. Cl. ........................................ 433/174; 433/175
(58) Field of Classification Search .......... 433/169–175; 521/149; 606/69
See application file for complete search history.

(56) References Cited

U.S. PATENT DOCUMENTS

| | | | | |
|---|---|---|---|---|
| 3,474,537 A * | 10/1969 | Christensen | ................. | 433/174 |
| 3,579,831 A * | 5/1971 | Stevens et al. | ................. | 433/174 |
| 3,790,507 A * | 2/1974 | Hodosh | ................. | 521/149 |
| 3,955,280 A * | 5/1976 | Sneer | ................. | 433/169 |
| 4,960,381 A * | 10/1990 | Niznick | ................. | 433/174 |
| 5,076,788 A * | 12/1991 | Niznick | ................. | 433/173 |
| 5,246,370 A * | 9/1993 | Coatoam | ................. | 433/173 |
| 5,281,140 A * | 1/1994 | Niznick | ................. | 433/172 |
| 5,564,925 A * | 10/1996 | Shampanier | ................. | 433/173 |
| 5,588,838 A * | 12/1996 | Hansson et al. | ................. | 433/173 |
| 5,890,902 A | 4/1999 | Sapian | | |
| 5,947,733 A * | 9/1999 | Sutter et al. | ................. | 433/173 |
| 5,984,681 A * | 11/1999 | Huang | ................. | 433/174 |
| 6,083,004 A * | 7/2000 | Misch et al. | ................. | 433/173 |
| 6,537,069 B1 * | 3/2003 | Simmons, Jr. | ................. | 433/173 |
| 6,663,388 B1 * | 12/2003 | Schar et al. | ................. | 433/173 |
| 7,108,510 B2 * | 9/2006 | Niznick | ................. | 433/173 |
| 7,160,109 B2 * | 1/2007 | Gervais et al. | ................. | 433/141 |

(Continued)

FOREIGN PATENT DOCUMENTS

CN 1163743 A 11/1997

(Continued)

*Primary Examiner* — Cris L Rodriguez
*Assistant Examiner* — Matthew Saunders
(74) *Attorney, Agent, or Firm* — Mei & Mark LLP

(57) ABSTRACT

A bionic dental implant includes a main root (1), a basal platform (2) and a platform bolt (3). The main root (1) includes a fixing root part (11), a neck part (12) located on the upper end of the fixing root part (11), and a mounting channel (13) located inside the main root (1). An aperture (21) is provided inside the basal platform (2). The platform bolt (3) communicates with the aperture (21) to make the basal platform (2) to be fixed on the main root (1). The main root (1) also includes at least one subsidiary root (4). The main root (1) has the same number of inclined holes (14) as the subsidiary root. The inclined holes (14) form a sharp angle with respect to the mounting channel (13) and communicates with it. The upper ends of the subsidiary roots (4) are fixed inside the inclined holes (14) of the main root.

14 Claims, 17 Drawing Sheets

U.S. PATENT DOCUMENTS

| | | | |
|---|---|---|---|
| 7,249,949 B2 * | 7/2007 | Carter | 433/173 |
| 7,338,286 B2 * | 3/2008 | Porter et al. | 433/173 |
| 7,484,959 B2 * | 2/2009 | Porter et al. | 433/173 |
| 7,806,693 B2 * | 10/2010 | Hurson | 433/174 |
| 2003/0194679 A1 * | 10/2003 | Odrich et al. | 433/173 |
| 2008/0118892 A1 * | 5/2008 | Adams | 433/174 |
| 2011/0117522 A1 * | 5/2011 | Verma et al. | 433/174 |

FOREIGN PATENT DOCUMENTS

| | | |
|---|---|---|
| JP | 11-318942 A | 11/1999 |
| JP | 2000-60872 A | 2/2000 |

* cited by examiner

BIONIC DENTAL IMPLANT

FIELD OF THE INVENTION

The invention relates to an artificial dental system, particularly to a bionic dental implant which is implanted into a jaw bone and serves as an artificial tooth root. Meanwhile, the invention also relates to a main root, a subsidiary root and an implanting method which are applied to the bionic dental implant.

BACKGROUND OF THE INVENTION

For the convenience and long-term stability of clinical application, currently, the implant body which is successfully used for so many times by dentists is a cylinder-cone-shaped rotation in-position type implant body which is similar to a natural-tooth-root shape. The shape is an axial-symmetrical-cylinder shaped implant body or a cone-shaped implant body. The surface of the implant body generally has screw threads which can be rotatably positioned at a bone hole of the prepared jaw bone. Therefore, certain initial-stage stability can be obtained. Furthermore, as various methods (such as surface coarsening and plasma spray coating) in which the same jaw bone biological contact area is increased on the surface of the implant body is implemented, the implant body is popularly used in the world currently.

The invention, which has publication No. CN1826089A and name of "dental implant", discloses a dental implant consisting of a fixing root part, a neck part and a basal platform part. The patent is a classic cylinder-cone-shaped rotation in-position type implant. As being a single-cylinder body or a cone-shaped body, the implant body can not form the mutual tensile action similar to that between a plurality of root teeth of a natural tooth so as to fulfill the anti-rotation and anti-twist function. Only the limited initial fixing action of the threads of the surface of an implant body can not resist various torque force interference produced on the implant body by the teeth on the base of the implant body when food is chewed. Therefore, currently, most of the implant bodies should wait several months after having been implanted into the jaw bone, and the teeth can not be mounted and stressed and can not implement chewing function; otherwise, the organic bone combination on the contact interface between the implant body and the jaw bone will be destroyed, and the implant body will eventually become loosened and the implanting will failed.

SUMMARY OF THE INVENTION

The invention relates to an artificial dental system, particularly to a bionic dental implant which is implanted into a jaw bone and serves as an artificial tooth root. Meanwhile, the invention also relates to a main root, a subsidiary root and an implanting method which are applied to the bionic dental implant.

One of the purposes of the invention is to provide a bionic dental implant similar to the natural tooth root so as to cover the shortages of the prior art. The bionic dental implant not only has good initial stable performance and initial anti-rotation and anti-twist function but also can increase the contact area between the implant body and the jaw bone and increase the success ratio of immediate stress and long-term stability and effectiveness after being implanted.

In order to obtain the above purposes, the technique scheme of the bionic dental implant of the invention is as follows:

A bionic dental implant comprises a main root, a basal platform and a platform bolt. The main root includes a fixing root part, a neck part located on the upper end of the fixing root part and a mounting channel located inside the main root. An aperture is provided inside the basal platform, the platform bolt communicates with the aperture to make the basal platform to be fixed on the main root. The invention is characterized in that the main root also includes at least one subsidiary root, the main root has the same number of inclined holes as the subsidiary root, the inclined holes form a sharp angle with respect to the mounting channel and communicate with it, and the upper end of the subsidiary root are fixed inside the inclined holes of the main root.

As one main embodiment of the invention, a mounting channel of a main root comprises a cone hole, a multi-square hole and a screw hole in the order from the top down. A basal platform comprises a basal platform part, a cone body located at the lower end of the basal platform part and matched with a cone hole and a multi-square body located at the lower end of the cone body and matched with the multi-square hole of the main root. The sides of the multi-square body of the basal platform are provided with a dovetail groove corresponding to the number of a subsidiary root. A dovetail joint matched with the dovetail groove on the multi-square body is provided on the end surface of the subsidiary root of the upper end of the subsidiary root. After the basal platform is inserted into the mounting channel, the dovetail groove on the basal platform and a dovetail joint on the subsidiary root are clamped together. The subsidiary root is fixedly mounted in an inclined hole of the main root. A mounting positioning hole is provided in the end surface of the subsidiary root.

As another embodiment of the invention, a mounting channel of a main root comprises a cone hole, a multi-square hole and a screw hole in the order from the top down. The basal platform comprises a basal platform part, a cone body located at the lower end of the basal platform part and matched with the cone hole of the main root and a multi-square body located at the lower end of the cone body and matched with the multi-square hole of the main root. The sides of the multi-square body of the basal platform are provided with a dovetail joint corresponding to the number of a subsidiary root. A dovetail groove matched with the dovetail joint on the multi-square body is provided on the end surface of the subsidiary root of the upper end part of the subsidiary root. A groove passed through the dovetail joint is provided inside of the multi-square hole of the main root. After the basal platform is inserted into the mounting channel, the dovetail joint on the basal platform and a dovetail groove of the subsidiary root are clamped with each other; therefore, the subsidiary root is fixed and mounted in an inclined hole of the main root. A mounting positioning hole is provided in the end surface of the subsidiary root.

As another main embodiment of the invention, a mounting channel of a main root comprises a cone hole, a multi-square hole and a screw hole. A basal platform comprises a basal platform part, a cone body located at the lower end of the basal platform part and matched with the cone hole of the main root and a multi-square body located at the lower end of the cone body and matched with the multi-square hole of the main root. The upper end part of a subsidiary root is a cone body. The cone body of the subsidiary root gradually becomes bigger along an axis toward the end surface of the subsidiary root. The end surface of the subsidiary root is a concave surface matched with the periphery surface of the cone body of the basal platform. A mounting positioning hole is provided at the end surface of the subsidiary root. The shape of an inclined hole of the main root is a cone hole matched with the cone body of the subsidiary root. After the basal platform is inserted into the mounting channel, the outer surface of the cone body of the basal platform contacts and is matched with the concave surface on the end surface of the subsidiary root. Therefore, the subsidiary root is fixed and mounted in the inclined hole of the main root.

Another purpose of the invention aims at covering the shortages of the prior art and provides a main root applied to a bionic dental implant. The concrete technique scheme is as follows:

The main root is provided with at least an inclined hole. The inclined holes form a sharp angle with respect to a mounting channel and communicate with it. Therefore, the upper end of a subsidiary root is fixed and mounted in the inclined hole of the main root.

Another purpose of the invention aims at covering the shortages of the prior art and provides a subsidiary root of a bionic dental implant. The concrete technique scheme is as follows:

The outer diameter of the upper end of a subsidiary root is matched with the inner diameter of the inclined hole. Therefore, the upper end of the subsidiary root is fixed and mounted in the inclined hole of the main root.

Another purpose of the invention aims at covering the shortages of the prior art and provides an implanting method applied to a bionic dental implant. The concrete technique scheme is as follows:

(1) A hole is drilled by a drilling tool in a jaw bone which is needed to be implanted in advance;

(2) The inner wall of a bone hole is threaded by a threading tool, and a thread hole matched with the outer thread of the main root is formed;

(3) Multi-square holes are connected with each other by a tool. The main root is screwed into the bone hole;

(4) A small drilling tool of which the diameter is mated with the subsidiary root is passed through a mounting channel and a inclined hole and reaches a jaw bone. The hole is drilled obliquely. The drilling depth is the same as the depth by which the subsidiary root is implanted into a jaw bone;

(5) After mounting positioning holes are connected with each other by a mounting positioning tool, a subsidiary root is passed through a mounting channel and a inclined hole and reaches a bone hole, which guarantees the end surface of the subsidiary root and the sides of a multi-square hole of a main root are positioned at the same plane;

(6) A basal platform is placed downwards from a mounting channel. A dovetail groove or a dovetail joint of the sides of a multi-square body is smoothly inserted, is combined with the dovetail joint or the dovetail groove of a subsidiary root and forms a tight tabling. The subsidiary root is fixed and mounted in a inclined hole of a main root;

(7) A bolt of a basal platform is winded up and the above parts form a tight integration one.

The advantages of the invention are that a bionic dental implant of the invention forms at least a multi-dental implant body fixing system which has more than two fixing roots; therefore, it not only forms multi-root plane type resistance distribution which fulfills the tensile action between the roots and resists the chewing and rotation interference but also forms a multi-root steric type resistance distribution. It embodies the physiological feature of the natural tooth of "the bigger the area between the tooth roots is, the more stable the teeth are". It obviously enhances the initial stability of the implant body. The mutual tensile action between the multi-roots stimulates the bone fibers of a jaw bone, which better accords with the physiological feature of the jaw bone. Therefore, the invention has the advantages of more bone tissue hyperplasia, less absorption and effective enhancement of the combination of the implant body and the bone tissue.

Furthermore, through the change of the angle between a main root and a subsidiary root, the scope of shape of a bionic dental implant almost comprises the shapes of the tooth root structures of various natural teeth. Therefore, the stressed method and the resistance method of the dental implant are more similar to that of the natural physiological status of the natural teeth. As the intersecting implanting method of a subsidiary root and a main root, the lengths, sizes, direction and intersecting parts, intersecting angle of the subsidiary root and the main root, and the inclined angle of the whole implant body can be selected flexibly according to the status, texture, anatomical structure conditions of the bone in the implanted area of a jaw bone before the operation when the bionic dental implant is implanted. Therefore, multiple roots of a steric combinative structure in multiple planes are formed. The potential implanting space in the jaw bone is further widened. Meanwhile, non-damage anatomical structures on the jaw bone such as tubes, cavities and sinuses can be avoided, and the implanting adaptation scope can be widened.

Furthermore, the invention has good initial stability performance and initial anti-rotation and anti-twist performance. It can increase the contacting area between an implant body and a jaw bone. It also increases the success ratio of immediate stress after the implanting and the success ratio of stably fulfilling the chewing action for long term. Particularly, compared with the single implant body of the prior art, because the implanting position of a subsidiary root is more biased toward the inner side and/or the outer side of a jaw bone, the subsidiary root is implanted in cortical bone. And, the subsidiary root is connected with the main root, in which the fixing root part is part of the main root. Therefore, the fixing root part of the implant body is easier to be implanted in the cortical bone in higher bone density and is obliquely and rotatably fixed in the cortical bone, which can obtain bigger fixing force of the high-density bone. Therefore, compared with the single implant body of the prior art and the implant body one part of surface of or most of the surface of which is positioned in the spongy bone with less bone density, the invention has remarkable and good initial stability. Meanwhile, the intersecting implanting technique of multiple roots of the invention effectively embodies the biomechanical features of mutual tension, mutual support and commonly resisting the resolution of the lateral torque force when the chewing force is held between a plurality of the dental roots of natural teeth. Therefore, it not only increases the initial stressing level of the implant body but also has the material base for decreasing the absorption which is formed by the torque force interference conducted in the sclerotin on the implant body interface of the jaw bone. The implanting method of a bionic dental implant is the same as the existing implanting operation, which is operated through an implanting port; furthermore, the implanting method of axially rotation entering positioning is both adopted by a main root and a subsidiary root. Therefore, the invention maintains the advantages of the simple operation and better practicability of the operation method when the dental implant is implanted into the jaw bone, and obtains the obvious advantages of the implanting of multiple roots.

Figure 1:
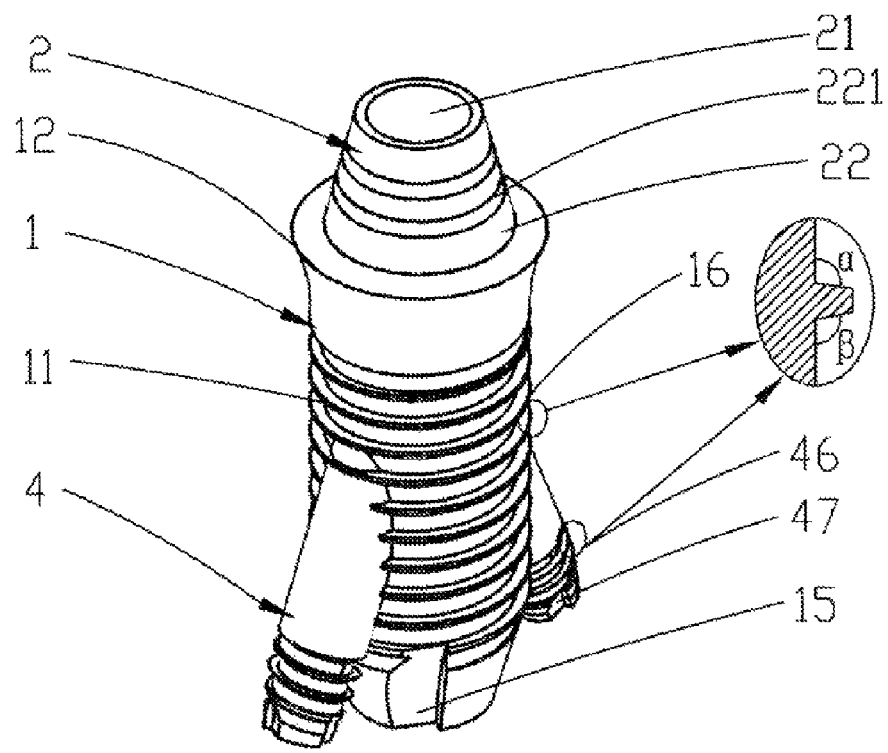
FIG. 1 shows a spatial view of an overall structure according to the embodiment 1 of the invention.
Figure 2:
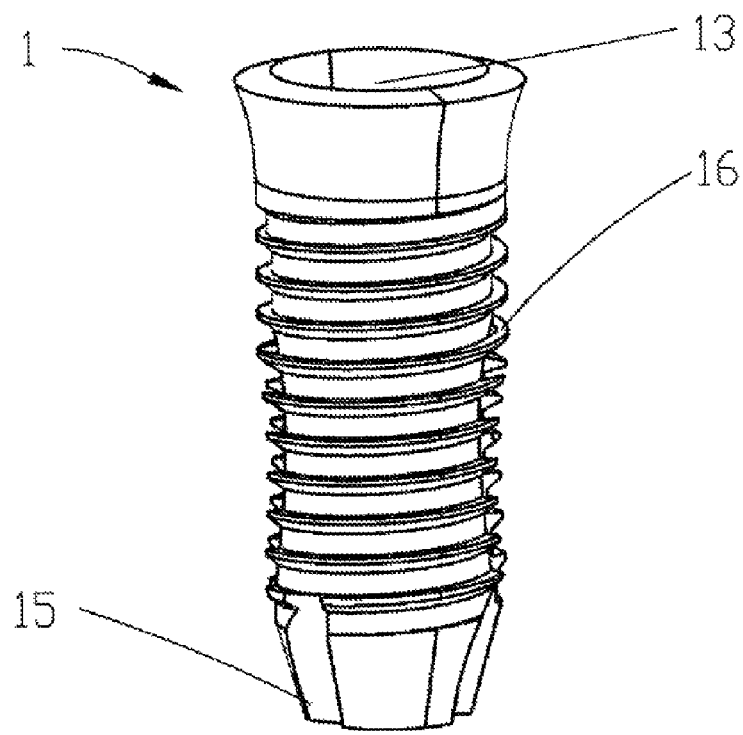
FIG. 2 shows a spatial view of a main root according to the embodiment 1 of the invention.
Figure 3:
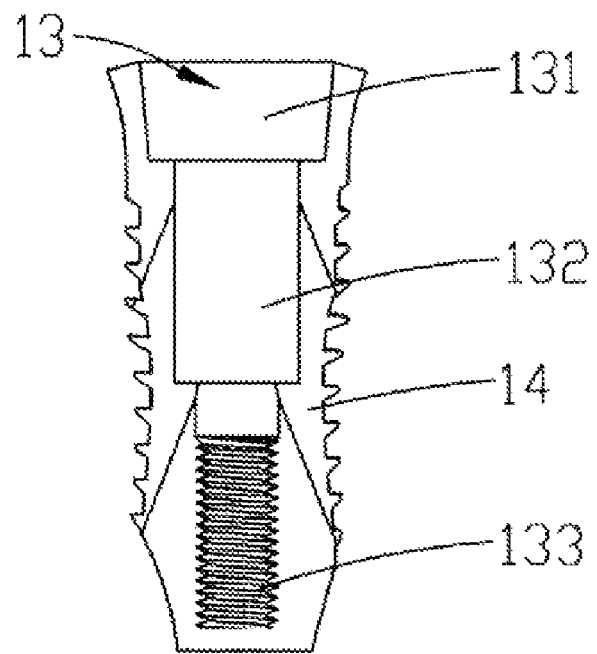
FIG. 3 shows a sectional view of FIG. 2.
Figure 4:
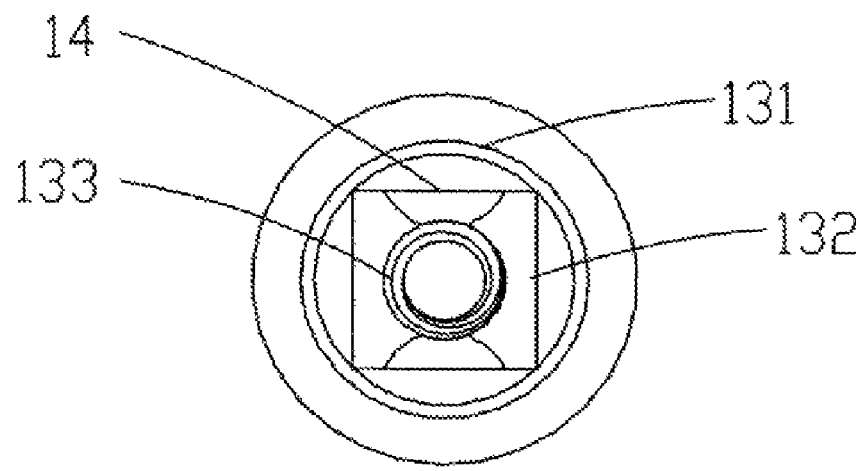
FIG. 4 shows a vertical view of FIG. 2.
Figure 5:
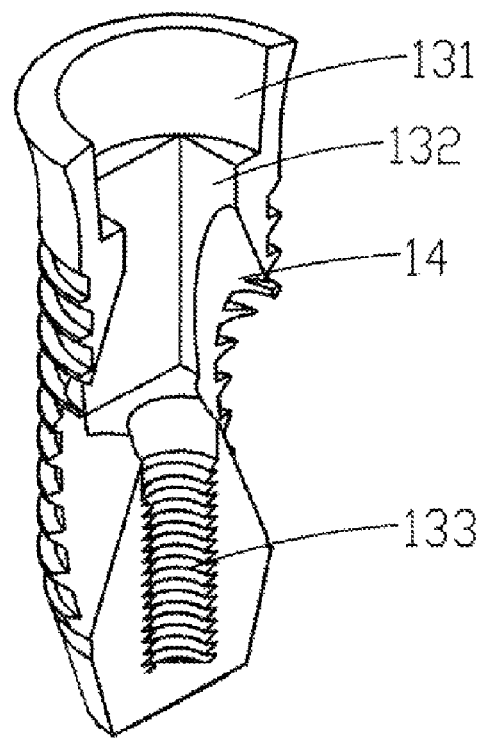
FIG. 5 shows a spatial view of the inner structure after the cut of FIG. 2.
Figure 6:
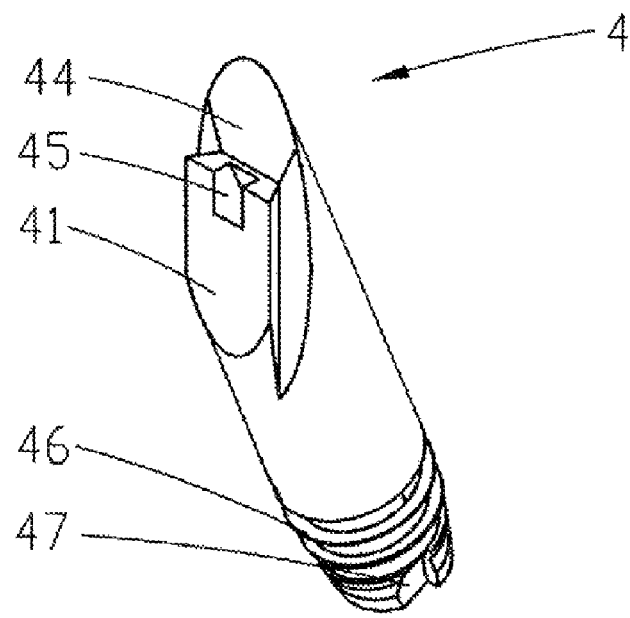
FIG. 6 shows a spatial view of a subsidiary root according to the embodiment 1 of the invention.
Figure 7:
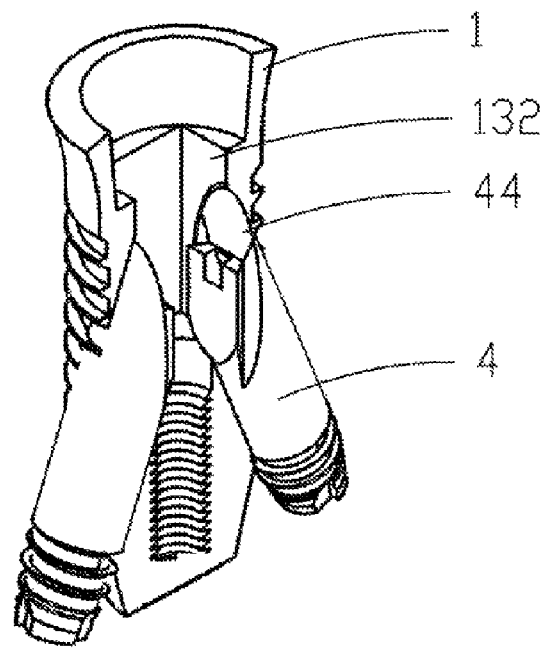
FIG. 7 shows a spatial view of the inner structure after the assembly of a main root and a subsidiary root according to the embodiment 1 of the invention.
Figure 8:
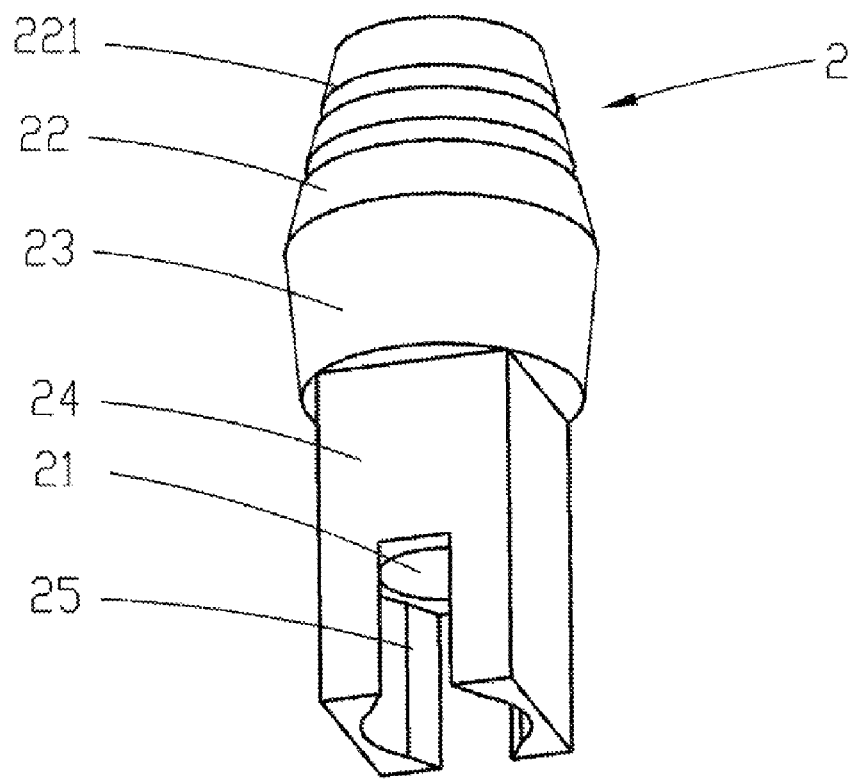
FIG. 8 shows a spatial view of a basal platform according to the embodiment 1 of the invention.
Figure 9:
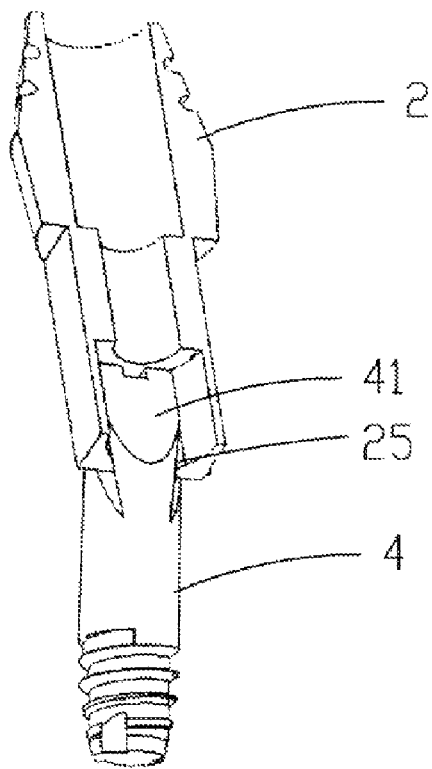
FIG. 9 shows a spatial view of the mutual tabling of a subsidiary root and a main root according to the embodiment 1 of the invention.
Figure 10:
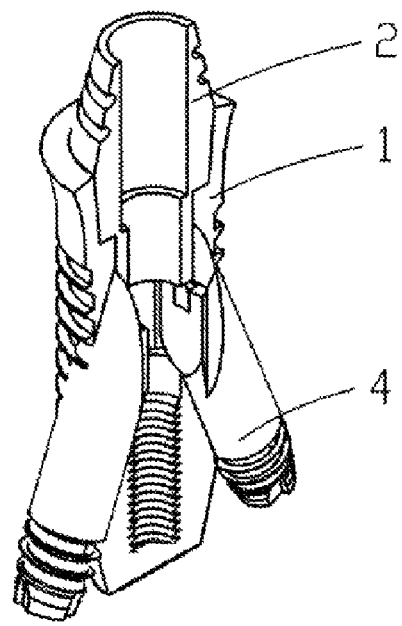
FIG. 10 shows a spatial view of the inner structure after the assembly of a main root, a subsidiary root and a basal platform according to the embodiment 1 of the invention.
Figure 11:
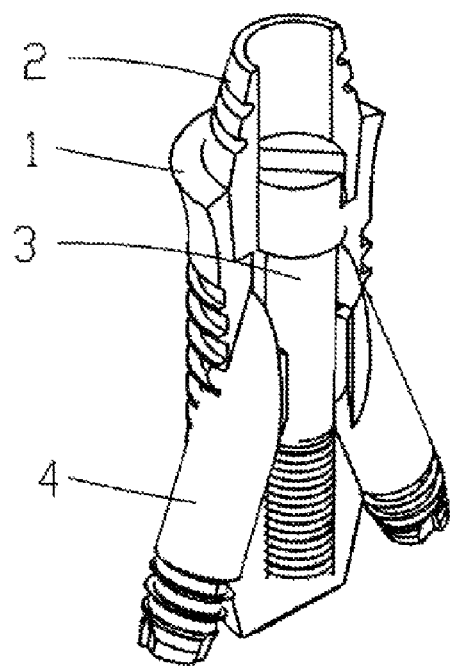
FIG. 11 shows a spatial view of the inner structure after the assembly of a main root, a subsidiary root, a basal platform and a basal platform bolt according to the embodiment 1 of the invention.
Figure 12:
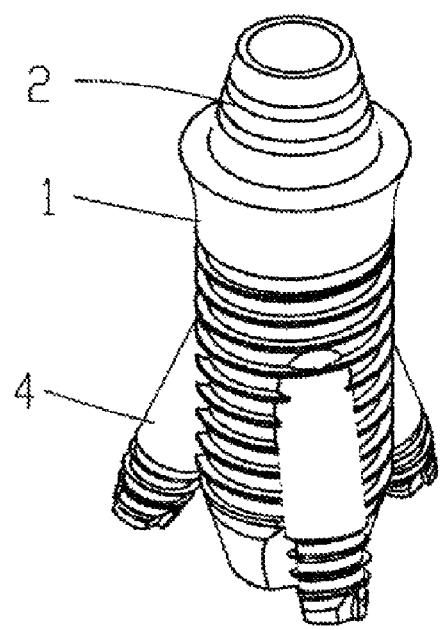
FIG. 12 shows a spatial view of an overall structure according to the embodiment 2 of the invention.
Figure 13:
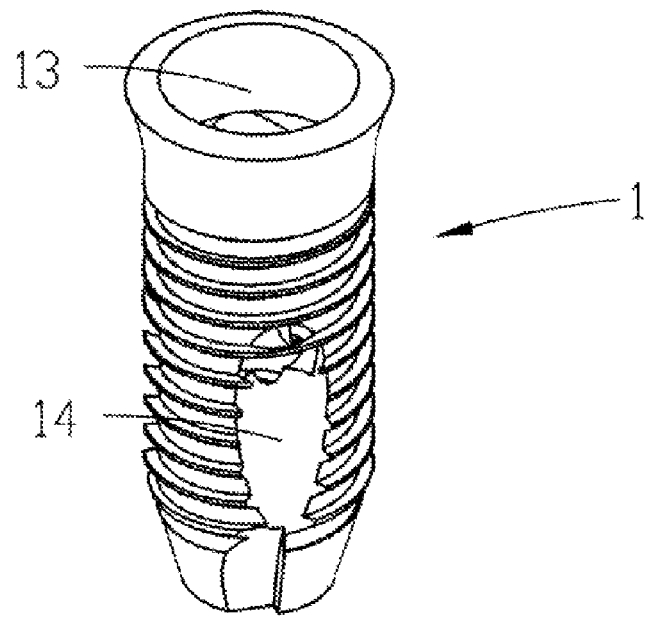
FIG. 13 shows a spatial view of a main root according to the embodiment 2 of the invention.
Figure 14:
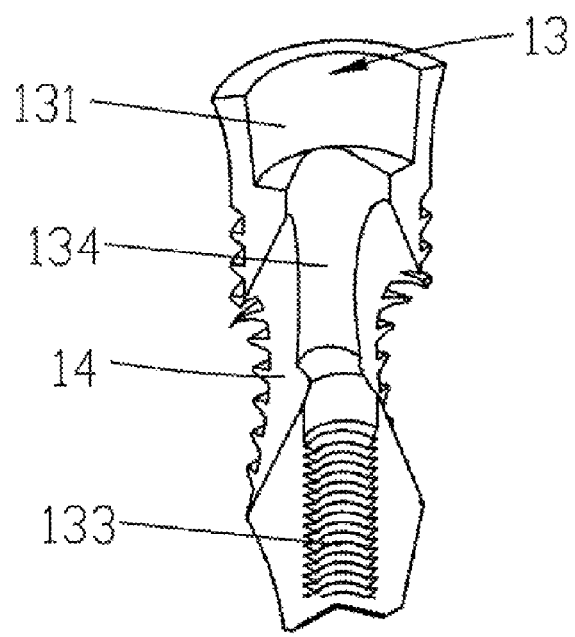
FIG. 14 shows a sectional view of FIG. 13.
Figure 15:
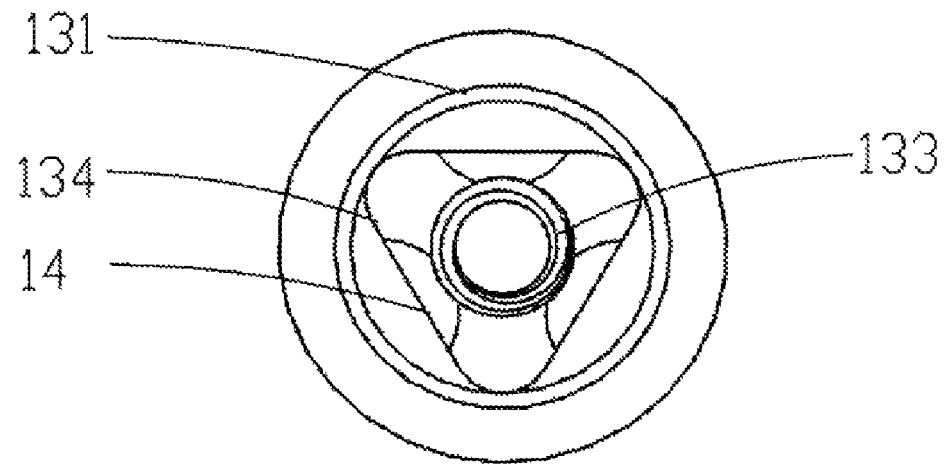
FIG. 15 shows a vertical view of FIG. 13.
Figure 16:
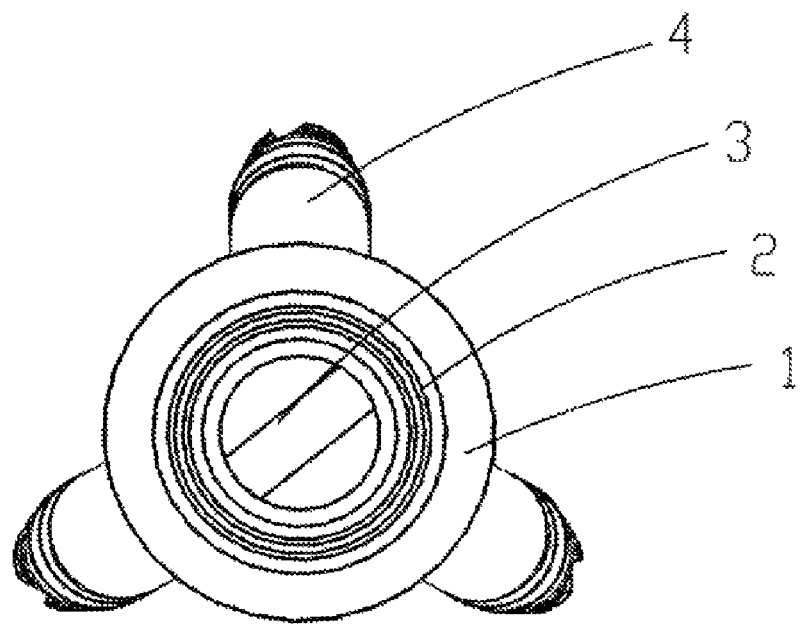
FIG. 16 shows a vertical view of FIG. 12.
Figure 17:
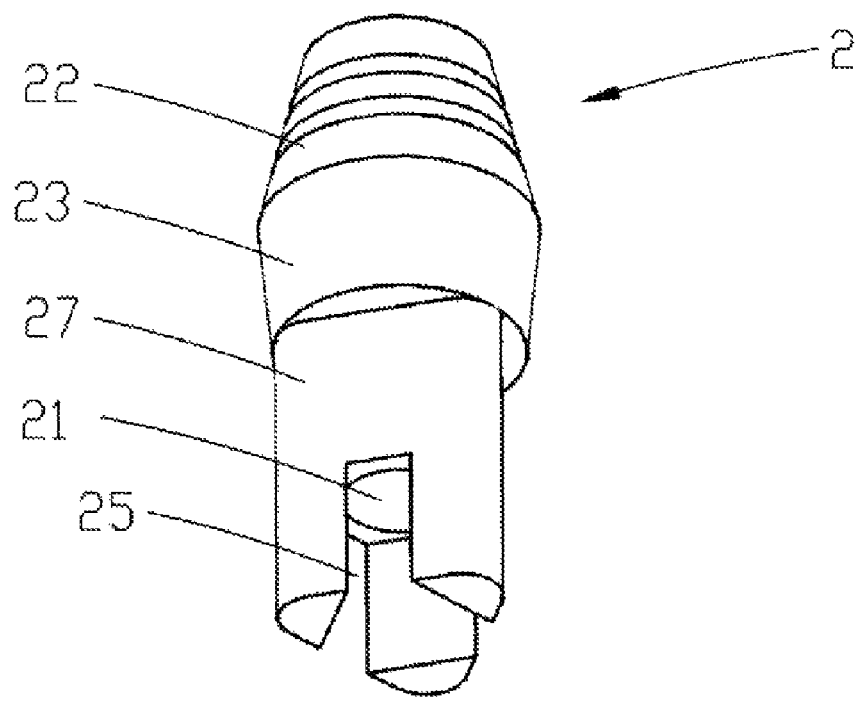
FIG. 17 shows a spatial view of a basal platform according to the embodiment 2 of the invention.
Figure 18:
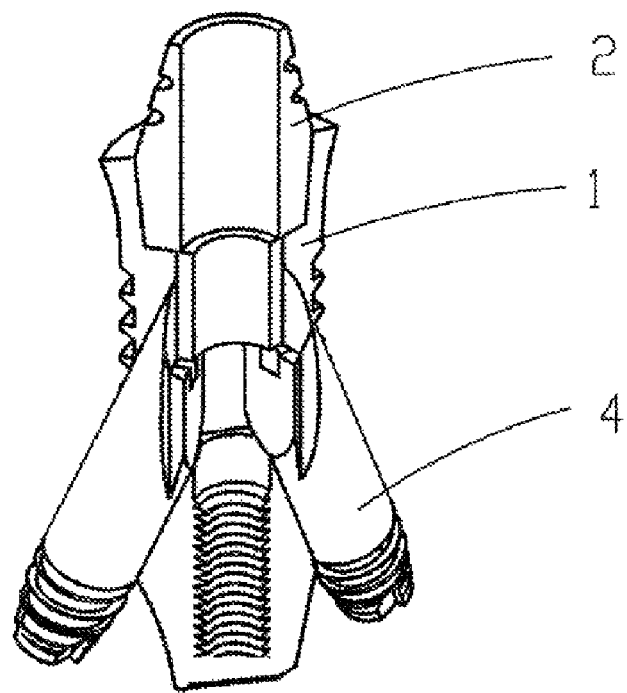
FIG. 18 shows a spatial view of the inner structure after the assembly of a main root, a subsidiary root and a basal platform according to the embodiment 2 of the invention.

Label Declaration Section: main root 1, fixing root part 11, neck part 12, mounting channel 13, cone hole 131, square hole 132, screw hole 133, trigonal hole 134, groove 135, inclined hole 14, leaf-shaped cut groove 15, screw thread 16, basal platform 2, aperture 21, basal platform part 22, basal platform groove 221, cone body 23, square body 24, dovetail groove 25, dovetail joint 26, trigonal body 27, basal platform bolt 3, subsidiary root 4, dovetail joint 41, dovetail groove 42, cone body 43, subsidiary root end surface 44, mounting positioning hole 45, screw thread 46, leaf-shaped cut groove 47, artificial tooth 5, tooth sinew 6 and jaw bone 7.

Embodiments:

With the figures, the preferred embodiments of the invention are further described as the following:

Embodiment 1

Referring to FIGS. 1, 2, 3, 4, 5, 6, 7, 8, 9, 10, 11 and 25, a bionic dental implant comprises a main root 1, a basal platform 2 and a basal platform bolt 3. The diameter of the main root 1 is 4.8 mm. The main root 1 comprises a fixing root part 11, a neck part 12 located at the upper end of the fixing root part 11 and a mounting channel 13 located inside the main root 1. An aperture 21 communicated with the two ends of the basal platform 2 is provided inside the basal platform 2. The basal platform bolt 3 is passed through the aperture 21 and fixes and mounts the basal platform 2 at the main root 1. The dental implant also comprises two subsidiary roots 4. The diameter of the subsidiary root 4 is 2 mm. The main root is provided with two inclined holes 14. The inclined holes 14 form a sharp angle with respect to the mounting channel 13 and communicate with it. The outer diameter of the upper end of the subsidiary hole 4 is matched with the inner diameter of the inclined hole 14 and is fixed and mounted in the inclined hole 14 of the main root. The included angle of the subsidiary root 4 and the main root 1 is 21 degrees.

The mounting channel 13 of the main root 1 comprises a cone hole 131, a square hole 132 and a screw hole 133 in the order from the top down. A basal platform 2 comprises a basal platform part 22, a cone body 23 located at the lower end of the basal platform part 22 and matched with the cone hole 131 of the main root 1 and a square body 24 located at the lower end and matched with a square hole 132 of the main root 1. The cone hole 131 becomes thinner from the top down. The sides of the square body 24 of the basal platform 2 are provided with two symmetrical dovetail grooves 25. The end surface 44 of the subsidiary root of the upper end part of the subsidiary root 4 is provided with a dovetail joint 41 matched with the dovetail groove 25 on the square body 24. The subsidiary root 4 and the basal platform 2 can be automatically locked after the dovetail groove 25 and the dovetail joint 41 are clamped together. Therefore, the subsidiary root is fixed and mounted in an inclined hole 14 of the main root 1. A mounting positioning hole 45 is provided in the end surface 44 of the subsidiary root. The shape of the mounting positioning hole 45 is a square hole. After a mounting tool and the mounting positioning hole 45 are connected together, the subsidiary root 4 can be positioned in a bone hole and be winded up.

Referring to FIG. 1, the lower end parts of the outer peripheries of a main root 1 and a subsidiary root 4 are provided with threads 16, 46. The section shapes of ridges of the threads are unsymmetrical trapezoids. The angle (α) between the upper end surfaces of the ridges and the axes of the main root 1 and the subsidiary root 4 are 102 degrees. The angle (β) between the lower end surfaces of the ridges and the axes of the main root and the subsidiary root is 123 degrees. Three leaf-shaped cut grooves 15, 47 are evenly distributed at the position close to the end surfaces of the threads 16, 46.

The basal platform part 22 of the basal platform 2 is also provided with a plurality of ring-shaped basal platform grooves 221, which offers convenience for an artificial tooth 5 to be stably mounted on the basal platform part 22.

An implanting method of a dental implant according to the embodiment 1 is as follows:

(1) A jaw bone 7 which is determined to be implanted in advance is drilled by a drilling tool;

(2) The inner wall of a bone hole is tapped by a tapping tool, and a tread hole matched with an outer thread 16 of a main root 1 is formed;

(3) Square holes 132 are connected by a tool. The main root 1 is screwed in the bone hole;

(4) A small drilling tool of which the diameter is matched with a subsidiary root is passed through a mounting channel 13 and an inclined hole 14 and drilled obliquely in a jaw bone. The depth of the drilling is the same as the implanting depth of the subsidiary root in the jaw bone;

(5) After a mounting positioning hole 45 of a subsidiary root 4 is connected by a mounting positioning tool, the subsidiary root 4 is passed through the mounting channel 13 and the inclined hole 14 and screwed into a bone hole. The end surface 44 of the subsidiary root and the sides of the square hole 132 of the main root 1 are guaranteed to be in the same plane;

(6) The basal platform 2 is placed downwards from a mounting channel 13. The dovetail groove 25 of the sides of the square body 24 is smoothly inserted downwards, is clamped with the dovetail joint 41 and forms the tight tabling. The subsidiary root 4 is fixed and mounted in the inclined hole 14 of the main root 1.

(7) The basal platform bolt 4 is winded up so that the above parts can be a tight integration one.

Embodiment 2

Referring to FIGS. 12, 13, 14, 15, 16, 17 and 18, the embodiment 1 is taken as reference. The same parts are not described repeatedly. The different part is that the number of a subsidiary root 4 becomes three, and the number of the inclined hole 14 on the corresponding main root 1 is changed from two to three. A square hole 132 of the main root 1 becomes a trigonal hole 134. A square body 24 of the basal platform 2 becomes a trigonal body 27. The number of the dovetail grooves 25 becomes three, which is respectively positioned on the three sides of the trigonal body 27.

Embodiment 3

Figure 19:
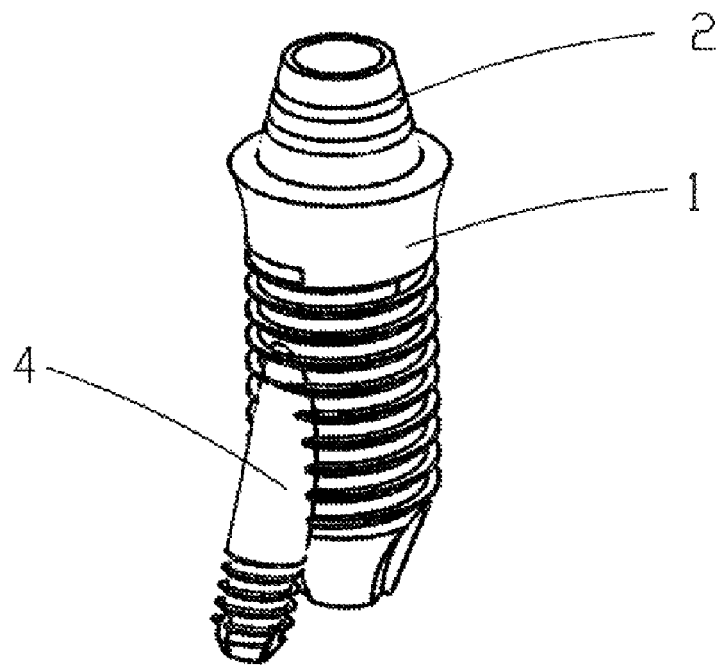
FIG. 19 shows a spatial view of an overall structure according to the embodiment 3 of the invention.

Referring to FIG. 19, the embodiment 1 is taken as reference. The same parts are not described repeatedly. The different part is that the number of the subsidiary root 4 becomes one. The number of inclined holes 14 of the corresponding main root 1 is changed from two to one. The number of a dovetail groove 25 on a square body 24 becomes one. The angle between the main root 1 and the subsidiary root 4 becomes 13 degrees.

Embodiment 4

Figure 20:
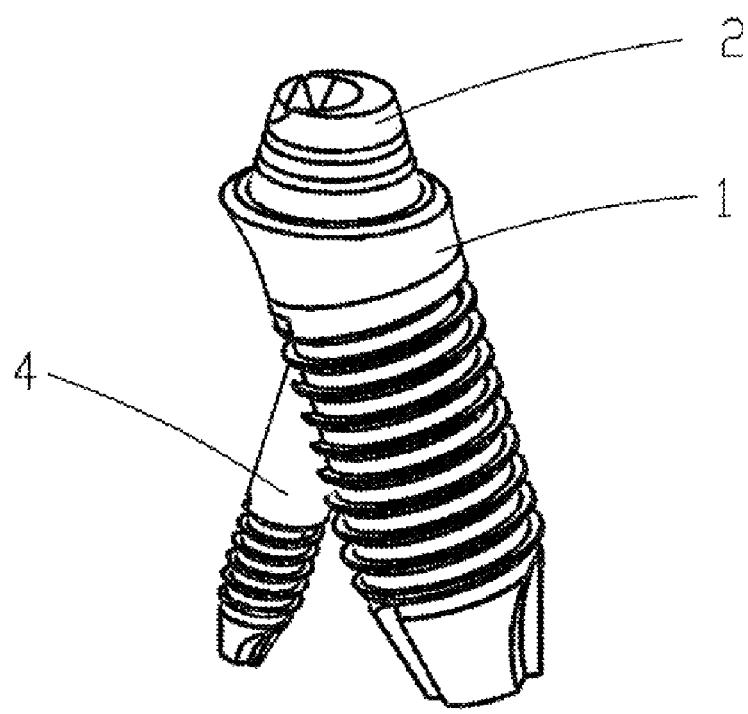
FIG. 20 shows a spatial view of an overall structure according to the embodiment 4 of the invention.

Referring to FIG. 20, the embodiment 3 is taken as reference. The same parts are not described repeatedly. The different part is that a main root 1 is oblique. The corresponding mounted basal platform 2 in the main root 1 is also oblique. The oblique angle is the same as that of the main root. The crossing angle between the main root 1 and the subsidiary root 4 is 43 degrees.

Embodiment 5

Figure 21:
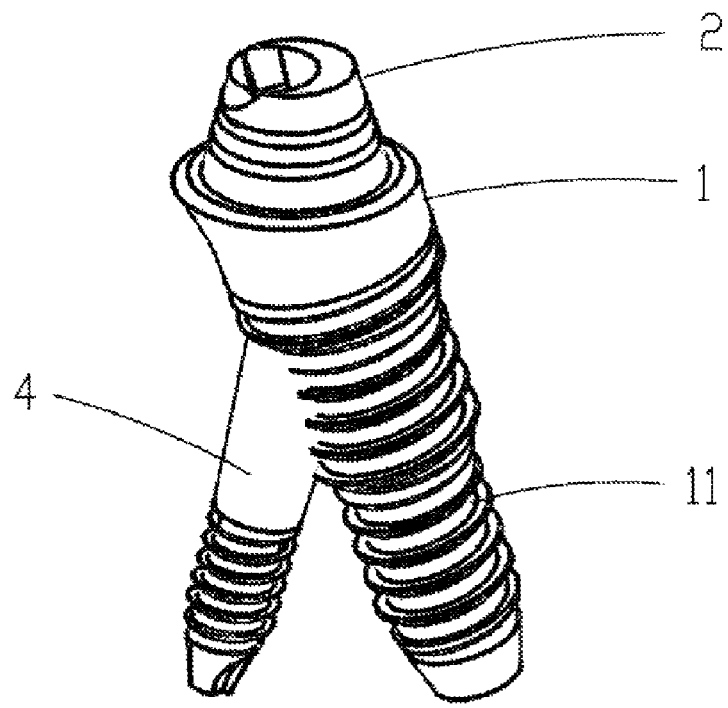
FIG. 21 shows a spatial view of an overall structure according to the embodiment 5 of the invention.

Referring to FIG. 21, the embodiment 4 is taken as reference. The same parts are not described repeatedly. The different part is that the lower end of a main root is in a cone shape and becomes smaller along the direction from a neck part 12 to a fixing root part 11.

Embodiment 6

Figure 22:
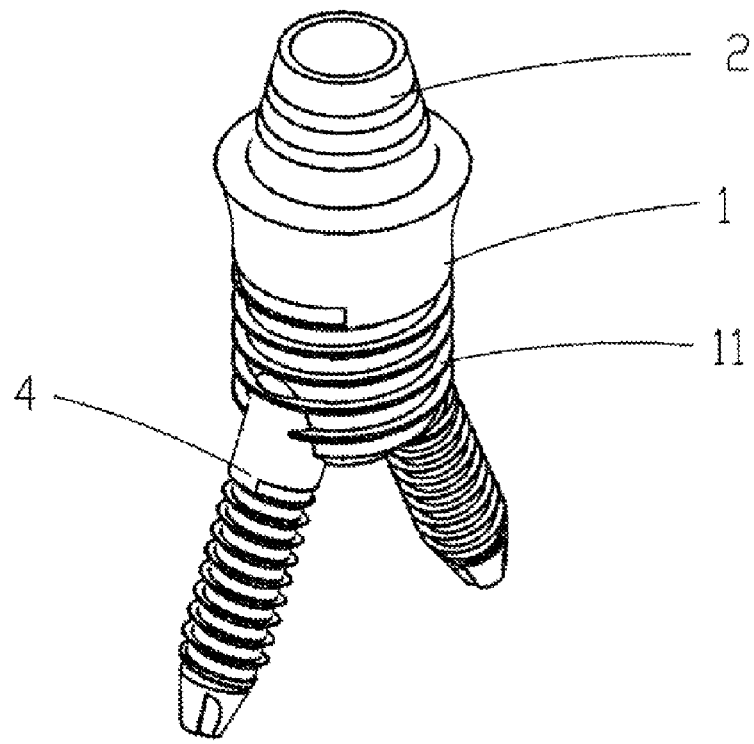
FIG. 22 shows a spatial view of an overall structure according to the embodiment 6 of the invention.

Referring to FIG. 22, the embodiment 1 is taken as reference. The same parts are not described repeatedly. The different part is that a main root is relatively short; i.e. the lower end of the main root 1 is obviously higher than the lower end surface of the subsidiary root 4. The included angle between the main root 1 and the subsidiary root 4 is 26 degrees.

Embodiment 7

Figure 23:
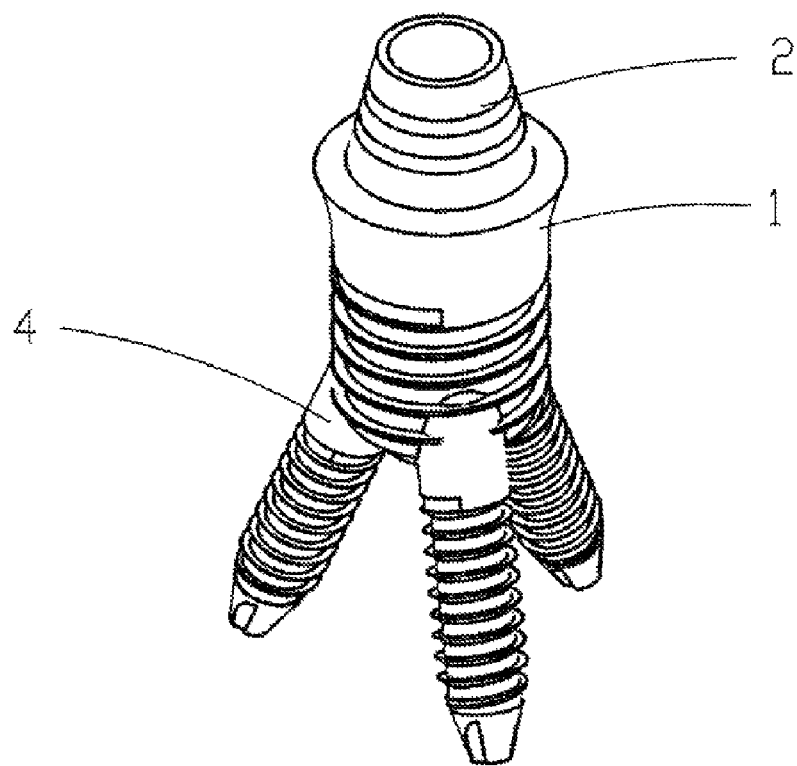
FIG. 23 shows a spatial view of an overall structure according to the embodiment 7 of the invention.

Referring to FIG. 23, the embodiment 2 is taken as reference. The same parts are not described repeatedly. The different part is that a main root 1 is relatively short; i.e. the lower end of the main root 1 is obviously higher than the lower end surface of a subsidiary root 4. The angle between the main root 1 and the subsidiary root 4 is 26 degrees.

Embodiment 8

Figure 24:
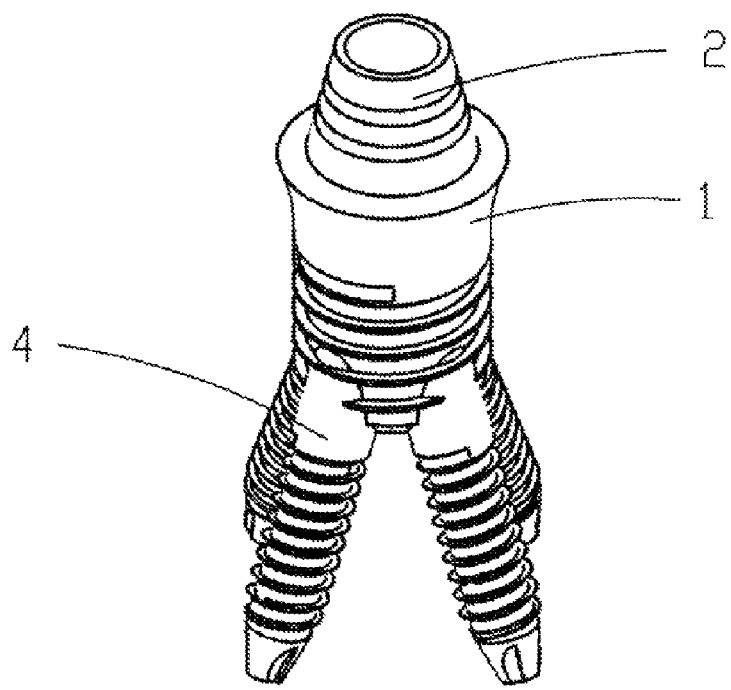
FIG. 24 shows a spatial view of an overall structure according to the embodiment 8 of the invention.

Referring to FIG. 24, the embodiment 6 is taken as reference. The same parts are not described repeatedly. The different part is that the number of subsidiary roots becomes four. The number of the inclined holes 14 on the corresponding main root 1 is changed from two to four. The number of the dovetail grooves 25 on a square body becomes four.

Embodiment 9

Referring to FIGS. 26, 27, 28 and 29, the embodiment 1 is taken as reference. The same parts are not described repeatedly. The different part is that the position of a dovetail groove 25 located on a square body 24 of a basal platform 2 is replaced with the position of a dovetail joint 41 on a subsidiary root 4. The dovetail joint 26 is arranged on the square body 24 of the basal platform. The dovetail groove 42 is arranged on the subsidiary root 4. Correspondingly, in order that the basal platform 2 can be inserted into a main root 1, the inside of a square hole 132 of the main root 1 is provided with a groove 135 which is passed through the dovetail joint 26.

After the dovetail groove 42 and the dovetail joint 26 of the embodiment are clamped together, the subsidiary root 4 and the basal platform 2 are automatically locked. Therefore, the subsidiary root 4 is fixed and mounted in the inclined hole 14 of the main root 1. The implanting method of the embodiment is the same as the embodiment 1. Therefore, it will not be described repeatedly.

Embodiment 10

Figure 30:
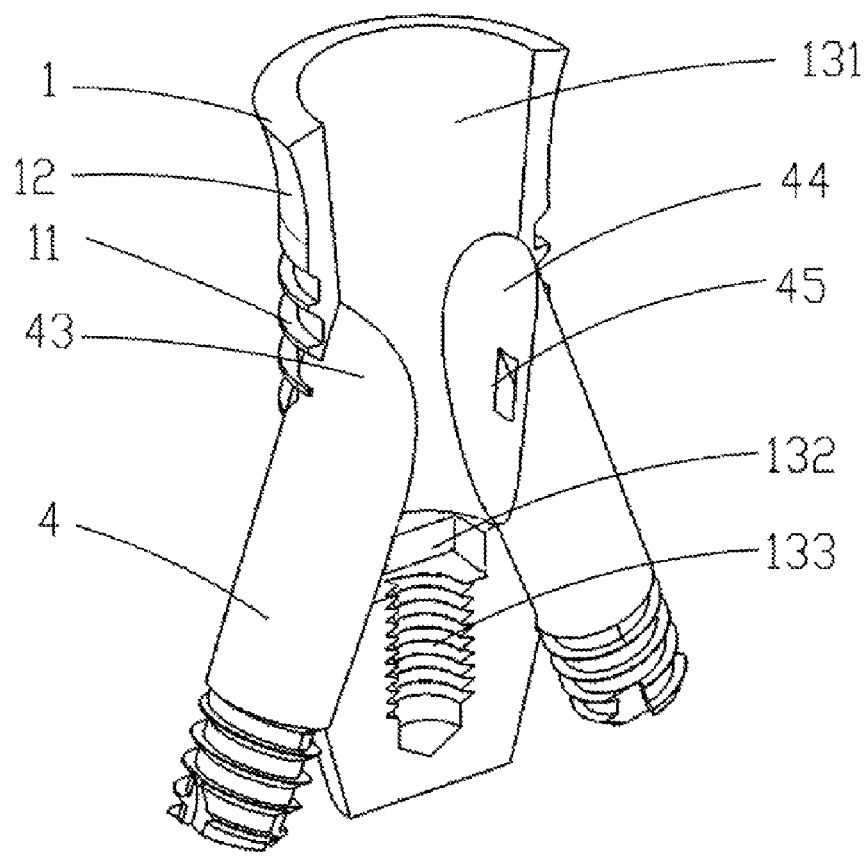
FIG. 30 shows a spatial view of the inner structure after the assembly of a main root and a subsidiary root according to the embodiment 10 of the invention.
Figure 31:
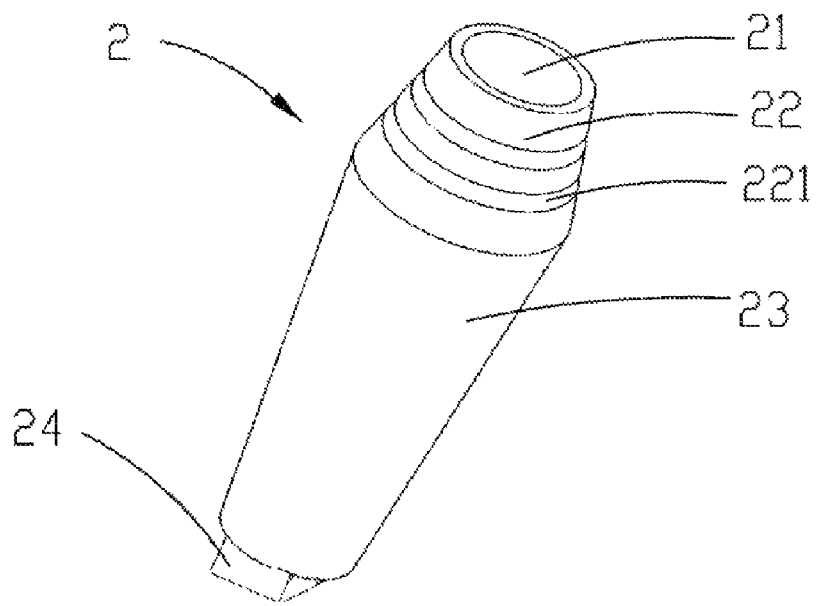
FIG. 31 shows a spatial view of a basal platform according to the embodiment 10 of the invention.
Figure 32:
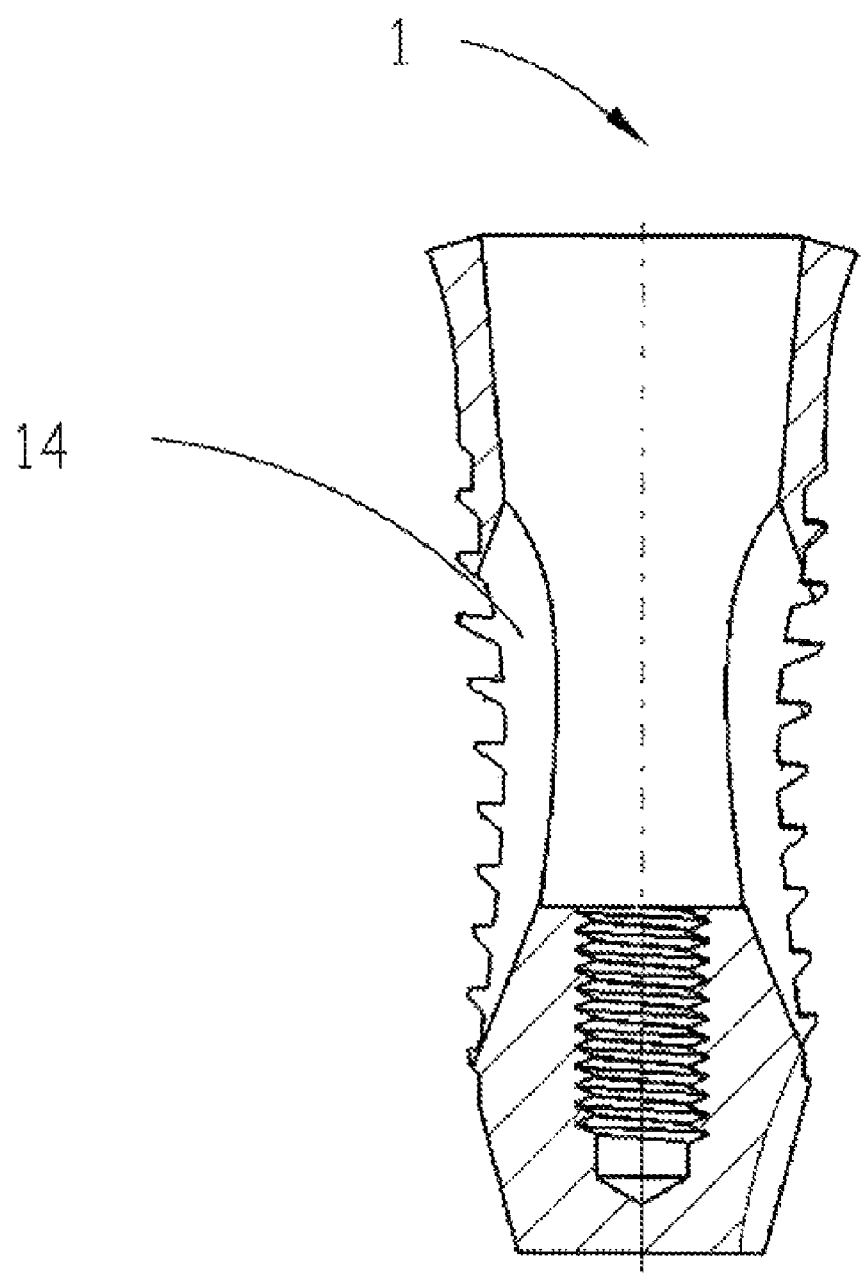
FIG. 32 is a sectional view of a main root according to the embodiment 10 of the invention.

Referring to FIGS. 30, 31 and 32, a mounting channel 13 of a main root 1 of a bionic dental implant comprises a cone hole 131, a multi-square hole 132 and a screw hole 133 in the order from the top down. A basal platform 2 comprises a basal platform part 22, a cone body 23 located at the lower end of the basal platform part 22 and matched with the cone hole 131 of the main root 1 and a square body 24 located at the lower end of the cone body 23 and matched with the square body 132 of the main root 1. The upper end part of the subsidiary root 4 is a cone body 43. The cone body gradually becomes bigger along the axial direction toward the end surface of the subsidiary root. The end surface 44 of the subsidiary root is a concave surface matched with the cone body 23 of the basal platform 2. The end surface 44 of the subsidiary root is provided with a mounting positioning hole 45. An inclined hole 14 of the main root 1 is a cone hole matched with the cone body 42 of the upper end part of the subsidiary root 4.

Embodiment 11

Based on any one of the embodiment 1 to embodiment 9, the widths of a dovetail groove 25, 42 and a dovetail joint 26, 41 gradually become bigger along the axial direction of a main root downwards so that a basal platform 2 can be easily placed in a mounting channel 13.

Embodiment 12

Based on any one of the embodiment 1 to embodiment 11, a multi-square hole of a main root 1 and the multi-square hole of a basal platform 2 gradually becomes thinner along the direction from a cone hole 131 to the multi-square hole.

Figure 25:
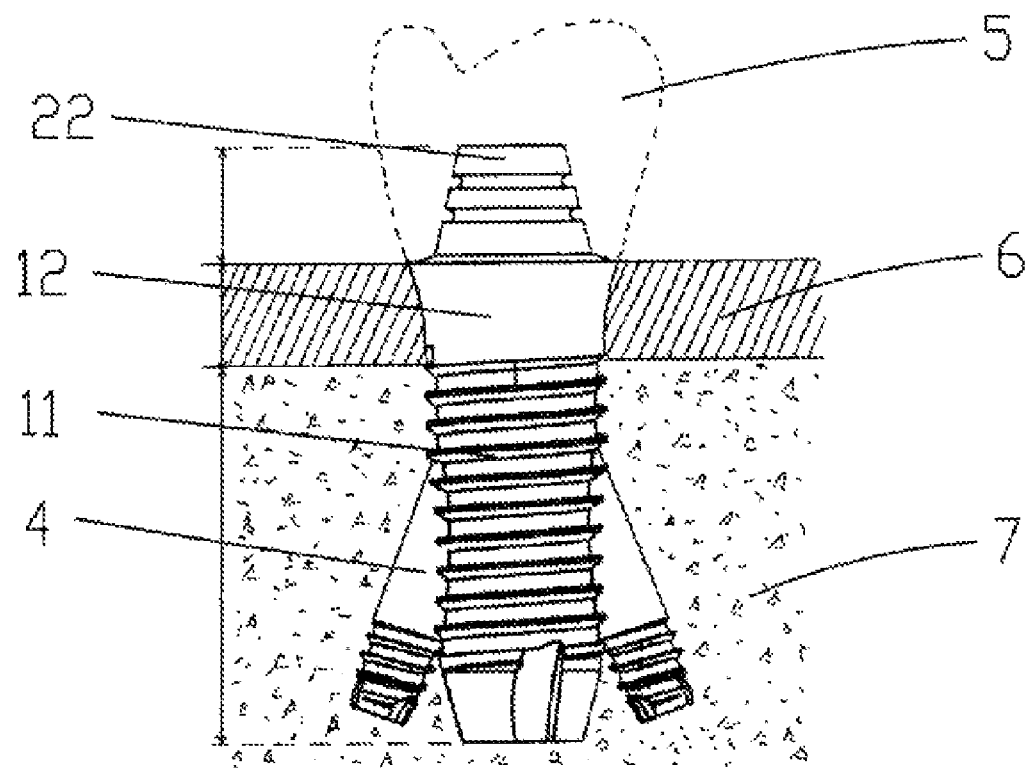
FIG. 25 shows a schematic diagram of the use state according to the invention.
Figure 26:
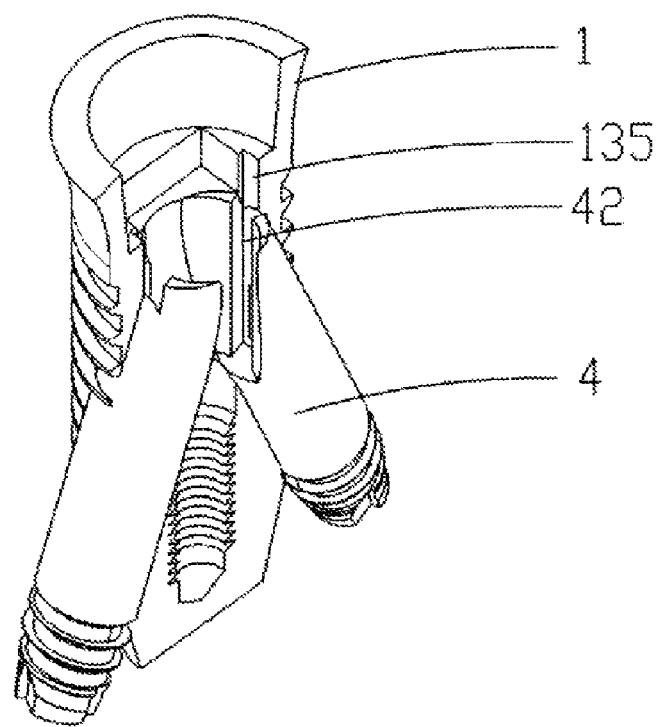
FIG. 26 shows a spatial view of the inner structure after the assembly of a main root and a subsidiary root according to the embodiment 9 of the invention.
Figure 27:
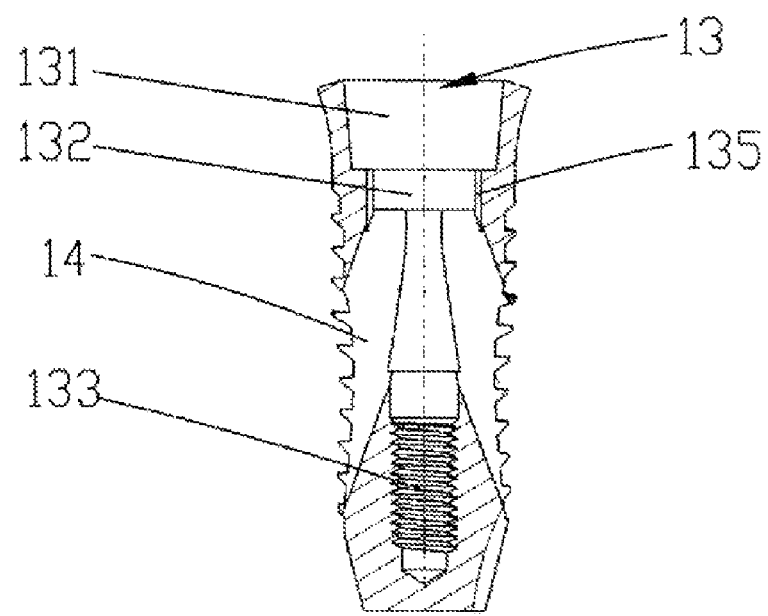
FIG. 27 shows a sectional view of a main root according to the embodiment 9 of the invention.
Figure 28:
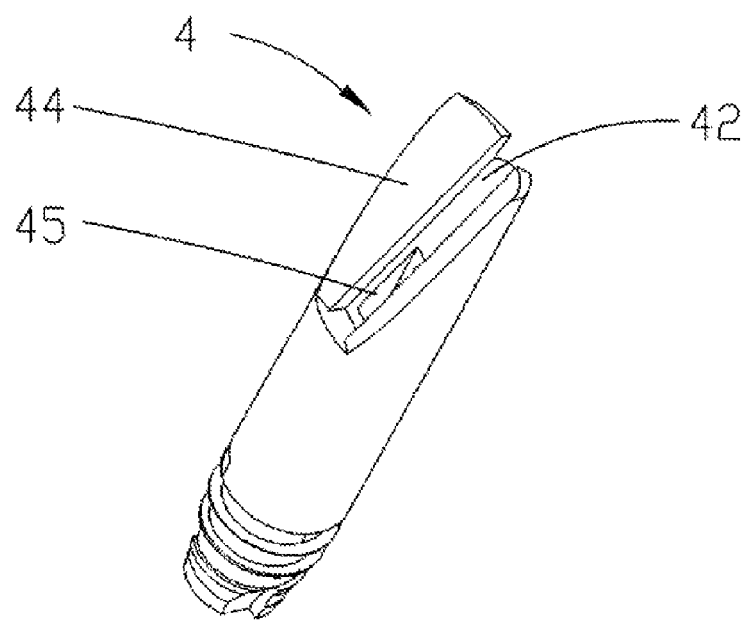
FIG. 28 shows a spatial view of a subsidiary root according to the embodiment 9 of the invention.
Figure 29:
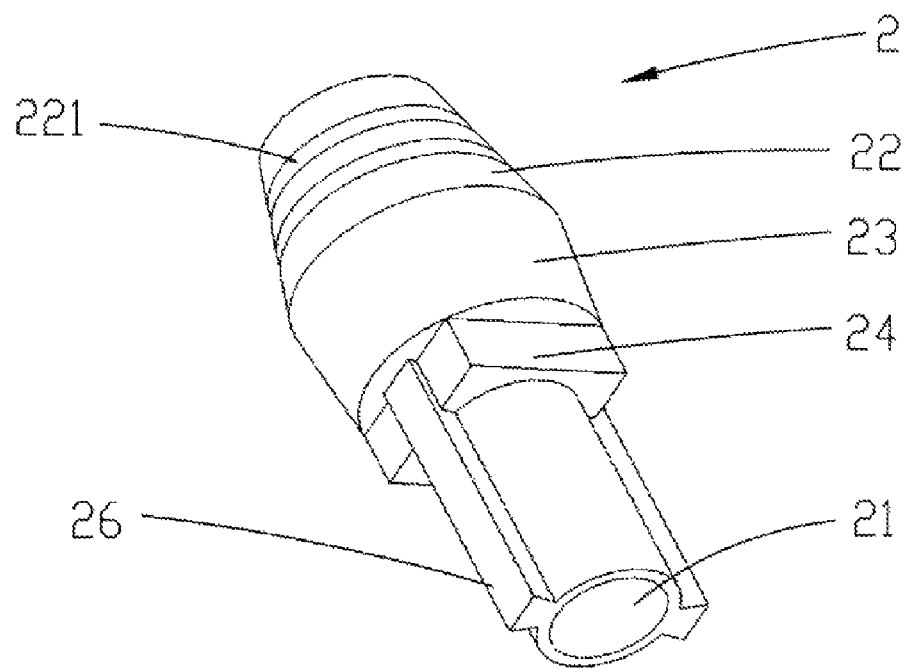
FIG. 29 shows a spatial view of a basal platform according to the embodiment 9 of the invention.

FIG. 25 is a mounting schematic diagram of a dental implant. From the figure, a fixing root part 11 of a main root 1 and a subsidiary root is mounted in a jaw bone 7. A neck part 12 of a main root 1 is mounted in a tooth sinew. A basal platform part 22 of a basal platform 2 protrudes from the tooth sinew. An artificial tooth 5 is mounted on the basal platform part 22. The main root 1 and the subsidiary root 4 can not be mounted in the jaw bone at the same time. After the main root must be mounted firstly, the subsidiary root is then mounted in an inclined hole 14 of the main root 1 through a mounting channel 13 in the main root 1. According to the medical requirement, the mounted main root 1 and the subsidiary root 4 must be stably connected with each other as an integration one. The subsidiary root 4 can not have displacement with respect to the inclined hole 14 of the main root 1. In order to obtain the above requirement of the function, the embodiment of the invention discloses that a dovetail groove 42 or a dovetail joint 41 matched with the dovetail joint 26 or the dovetail groove 25 on the basal platform is arranged at the end part of the subsidiary root. The structures of the dovetail groove 42 and the dovetail joint 41 meet the requirements of the above function. The invention also discloses that a cone body matched with the inclined hole of the main root 1 is arranged at the end part of the subsidiary root. Furthermore, the end surface of the cone body of the subsidiary root 4 forms the concave surface matched with the cone body 23 of the basal platform so as to meet the above requirements. However, the embodiments can not be understood that they are the limit of the invention. Every structure which can stably connect the main root 1 and the subsidiary root 4 as an integration one after the main root 1, the subsidiary root 4 and the basal platform 2 are assembled together belongs to the protection scope of the invention.

In the invention, the number of a subsidiary root can be flexibly selected according to the requirements, such as one, two, three, four and a plurality of the subsidiary roots. The mounting direction and the angle of the subsidiary root 4 also can be flexibly selected according to the requirements. As the limited space, specifications are not described one by one.

In the invention, the angle between a subsidiary root and a main root can be a sharp angle in the biggest scope theoretically. But in the practical application, the best scope of the angle is from 13 degrees to 26 degrees when a main root is upright; the best scope of the angle between the main root and the subsidiary root is from 26 degrees and 43 degrees when the main root is oblique.

In the invention, a square hole and a trigonal hole in a mounting channel of the main root 1 mainly offer convenience for the mounting of the main root. A multi-square-hole structure such as a pentagon hole and a hexagon hole can be adopted.

In the invention, the thread type of a main root and a subsidiary root and the included angle ($\alpha$), ($\beta$) can be flexibly selected according to the requirements.

In conclusion, the technicians of the field will know that the embodiments help the readers to understand the principles of the invention; therefore, it should be understood that the protection scope of the invention does not limit the specifications and the embodiments.

The invention claimed is:

1. A dental implant, comprising:
a main root comprising a fixing root part, a neck part located at an upper end of the fixing root part, a mounting channel located inside the main root, the mounting channel comprising at least a multi-square hole, a cone hole, at least one inclined hole forming an angle with respect to the mounting channel and communicating with the mounting channel, and a screw hole following the multi-square hole;
a basal platform with an inner part having an aperture with two ends, the basal platform further comprising a cone body, a basal platform part, and a multi-square body;
a basal bolt configured to pass through the aperture and fix the basal platform on to the main root; and
a subsidiary root with an upper end mounted in the inclined hole,
wherein:
the basal platform fixes the upper end of the subsidiary root in the inclined hole by mating the multi-square body to the multi-square hole and by mating the cone body to the cone hole,
the cone hole precedes the multi-square hole,
the cone body is located at a lower end and is configured to match to the cone hole,
the multi-square body is located at a lower end of the cone body,
the multi-square body further comprises at least one dovetail groove,
the upper end of the subsidiary root further comprises an end surface comprising a dovetail joint, and
the dovetail groove and the dovetail joint mate to fix the subsidiary root in the inclined hole.

2. The dental implant of claim 1, wherein the end surface further comprises a mounting positioning hole.

3. A dental implant, comprising:
a main root comprising a fixing root part, a neck part located at an upper end of the fixing root part, a mounting channel located inside the main root, the mounting channel comprising at least a multi-square hole, a cone hole, at least one inclined hole forming an angle with respect to the mounting channel and communicating with the mounting channel, and a screw hole following the multi-square hole;
a basal platform with an inner part having an aperture with two ends, the basal platform further comprising a cone body, a basal platform part, and a multi-square body;
a basal bolt configured to pass through the aperture and fix the basal platform on to the main root; and
a subsidiary root with an upper end mounted in the inclined hole,
wherein:
the basal platform fixes the upper end of the subsidiary root in the inclined hole by mating the multi-square body to the multi-square hole and by mating the cone body to the cone hole,
the cone hole precedes the multi-square hole,
the cone body is located at a lower end and is configured to match to the cone hole,
the multi-square body is located at a lower end of the cone body,
the multi-square body further comprises at least one dovetail joint,
the upper end of the subsidiary root further comprises an end surface comprising a dovetail groove, and
the dovetail groove and the dovetail joint mate to fix the subsidiary root in the inclined hole.

4. The dental implant of claim 3, wherein the end surface further comprises a mounting positioning hole.

5. The dental implant according to any one of claims 1 or 3, wherein a width of the dovetail groove and a width of the dovetail joint gradually become bigger along a longitudinal axial downward direction.

6. The dental implant of claim 1, wherein:
the cone hole, the multi-square hole, and a screw hole are arranged from a top end to a bottom end in the main root, a platform body, the cone body, and the multi-square body are arranged from a top end to a bottom end of the basal platform, the subsidiary root has a cone shape that tapers away from the upper end, and the upper end of the subsidiary root comprises a concave surface that abuts an outer peripheral surface of the cone body.

7. The dental implant according to any one of claim 1, 3 or 6, wherein the multi-square hole and the multi-square body gradually become thinner along a longitudinal direction from the cone hole to the multi-square hole.

8. The dental implant according to any one of claim 1, 3 or 6, wherein an included angle between the main root and the subsidiary root is between 13 degrees and 26 degrees.

9. The dental implant according to any one of claim 1, 3 or 6, wherein an outer diameter of the upper end of the subsidiary root matches an inner diameter of the inclined hole.

10. The dental implant of claim 1, wherein the subsidiary root is configured to implant in to a cortical bone.

11. A method for implanting a dental implant, comprising:
drilling a jaw bone with a drilling tool;
tapping an inner wall of the bone hole with a tapping tool to form a threaded hole that matches an outer thread of a main root;
connecting multi-square holes of the main root with a connecting tool;
screwing the main root in to the bone hole;
passing a small drilling tool through a mounting channel and an inclined hole in the main root, the small drilling tool having a diameter matched to a diameter of a subsidiary root;
obliquely drilling the jaw bone to a depth equal to a depth to which the subsidiary root will be implanted in a second bone hole;
mounting a positioning hole of the subsidiary root to a mounting tool;
passing the subsidiary root through the mounting channel and the inclined hole;
screwing the subsidiary root into the second bone hole;
aligning an end surface of the subsidiary root with a plane of a multi-square hole of the main root;
placing a basal platform downward in to the mounting channel;
aligning a dovetail groove on an end face of the subsidiary root with a dovetail joint on a multi-square body on the basal platform; and
screwing a basal bolt through the basal platform and in to the mounting channel.

12. The method of claim 11, wherein the second bone hole enters cortical bone, and at least a portion of the subsidiary root is screwed into the cortical bone.

13. A method for implanting a dental implant, comprising:
drilling a jaw bone with a drilling tool;
tapping an inner wall of the bone hole with a tapping tool to form a threaded hole that matches an outer thread of a main root;
connecting multi-square holes of the main root with a connecting tool;
screwing the main root in to the bone hole;
passing a small drilling tool through a mounting channel and an inclined hole in the main root, the small drilling tool having a diameter matched to a diameter of a subsidiary root;
obliquely drilling the jaw bone to a depth equal to a depth to which the subsidiary root will be implanted in a second bone hole;
mounting a positioning hole of the subsidiary root to a mounting tool;
passing the subsidiary root through the mounting channel and the inclined hole;
screwing the subsidiary root into the second bone hole;
aligning an end surface of the subsidiary root with a plane of a multi-square hole of the main root;
placing a basal platform downward in to the mounting channel;
aligning a dovetail joint on an end face of the subsidiary root with a dovetail groove on a multi-square body on the basal platform; and
screwing a basal bolt through the basal platform and in to the mounting channel.

14. The method of claim 13, wherein the second bone hole enters cortical bone, and at least a portion of the subsidiary root is screwed into the cortical bone.

* * * * *